(12) United States Patent
Xin et al.

(10) Patent No.: US 11,891,553 B2
(45) Date of Patent: Feb. 6, 2024

(54) SILVER NANOCLUSTER FLUORESCENT NANOTUBE, A PREPARATION METHOD AND ITS APPLICATION IN THE DETECTION OF ARGININE

(71) Applicant: SHANDONG UNIVERSITY, Jinan (CN)

(72) Inventors: Xia Xin, Jinan (CN); Wenjuan Wang, Jinan (CN); Di Sun, Jinan (CN); Zhi Wang, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 18/049,723

(22) Filed: Oct. 26, 2022

(65) Prior Publication Data
US 2023/0159820 A1    May 25, 2023

(51) Int. Cl.
| | |
|---|---|
| C09K 11/58 | (2006.01) |
| C09K 11/06 | (2006.01) |
| B82Y 15/00 | (2011.01) |
| B82Y 5/00 | (2011.01) |
| C01B 32/16 | (2017.01) |

(52) U.S. Cl.
CPC ............... C09K 11/58 (2013.01); B82Y 5/00 (2013.01); B82Y 15/00 (2013.01); C01B 32/16 (2017.08); C09K 11/06 (2013.01)

(58) Field of Classification Search
CPC .......... C09K 11/58; C09K 11/06; C01B 32/16
USPC ..................................................... 252/520.3
See application file for complete search history.

(56) References Cited

U.S. PATENT DOCUMENTS

2021/0396747 A1* 12/2021 Singamaneni ... G01N 33/54346

FOREIGN PATENT DOCUMENTS

| | | | |
|---|---|---|---|
| CN | 106880593 A | 6/2017 | |
| CN | 110132953 A | 8/2019 | |
| CN | 110330512 A | * 10/2019 | ............. B82Y 20/00 |
| CN | 110330512 A | 10/2019 | |
| CN | 111303868 A | 6/2020 | |

OTHER PUBLICATIONS

Sun "Self-Assembly-Driven Aggregation-Induced Emission of Silver Nanoclusters for Light Conversion and Temperature Sensing." ACS Appl. Nano Mater. 2020, 3, 2038-2046 (Year: 2020).*
Li "Facile preparation of silver nanocluster self-assemblies with aggregation-induced emission by equilibrium shifting." Nanoscale, 2021, 13, 14207 (Year: 2021).*

* cited by examiner

*Primary Examiner* — Tri V Nguyen
(74) *Attorney, Agent, or Firm* — CBM Patent Consulting, LLC

(57) ABSTRACT

A preparation process of atomically precise nine-nuclear silver nanoclusters ($Ag_9$-NCs) fluorescent nanotube and its application in the detection of arginine (Arg), the fluorescent nanotube is formed by supramolecular self-assembly of $Ag_9$-NCs and peptide (DD-5); the fluorescent nanotube prepared by the present invention has good luminescence performance due to its highly ordered structure, the quantum yield is 8.11%, and the fluorescence lifetime is 6.10 μs; after adding Arg, the highly ordered structure is destroyed, resulting in fluorescent quenching; the preparation method of the $Ag_9$-NCs fluorescent nanotube of this invention is simple, the cost is low; at the same time, the detection method is fast and easy to observe.

10 Claims, 6 Drawing Sheets

SILVER NANOCLUSTER FLUORESCENT NANOTUBE, A PREPARATION METHOD AND ITS APPLICATION IN THE DETECTION OF ARGININE

CROSS REFERENCES

This application claims priority to Chinese Patent Application Ser. No. CN202111420279.5 filed on 25 Nov. 2021.

FIELD

The present invention relates to a Silver nanocluster ($Ag_9$-NCs) fluorescent nanotube, preparation method and its application in the detection of arginine, belonging to the field of new materials.

BACKGROUND

It is well known that amino acids play an important role in the human body. Among various amino acids, arginine (Arg) also known as protein amino acid can stimulate the secretion of hormones such as insulin, growth hormone, glucagon, prolactin, etc., and help improve the health of the immune system and resist diseases. In this case of physical injury, the body's immune system is at its best, which can speed up the speed of the body's healing. In short, Arg plays an extremely important role in human growth and development, wound healing, and immune system. In addition, Arg content is also one of the key parameters to assess the pathophysiology of hyperammonemia and astrocyte and aggregated neural cell cultures. Therefore, it is crucial to develop a simple, fast, and easy-to-observe detection method to detect Arg.

In recent years, metal nanoclusters (NCs) have been widely used in the field of fluorescence sensing due to their low toxicity, low cost, good biocompatibility, and photoluminescence properties. As a kind of luminescent nanomaterials, NCs refer to metal cores composed of several to hundreds of metal atoms, and the surface of metal cores is generally modified by organic ligands, and its size is about the Fermi wavelength of electrons (<2 nm), by confining the vibration and rotation of ligands around the metal core and enhancing metallophilic interactions, strong fluorescence emission can be achieved, therefore NCs can be used as fluorescent probes to detect a variety of substances.

Silver nanoclusters (Ag NCs) are favored by people in the industry due to their special properties and wide range of raw material sources, there are also many reports on the patent documents of Ag NCs. Chinese patent document CN103940788A (application number: 201310017205.6) discloses a method for detecting hypochlorous acid by Ag NCs, which is characterized in that the Ag NCs are oxidized by hypochlorous acid to cause fluorescence quenching, using the Ag NCs solution as a fluorescent probe, the hypochlorous acid content was detected by fluorescence spectroscopy. Chinese patent document CN106053416A (application number: 201610554173.7) discloses a method for detecting $Fe^{3+}$ by Ag NCs, which is characterized in that the pH of the solution containing $Fe^{3+}$ is adjusted to be acidic, after adding Ag NCs for reaction, the pH of the solution is adjusted to neutrality, and the fluorescence intensity is detected by fluorescence spectrophotometer, then compare it with the standard curve of $Fe^{3+}$ concentration and fluorescence intensity, hence as to realize the detection of $Fe^{3+}$.

Chinese patent document CN112893864A (application number: 202110073160.9) discloses a method for preparing Ag NCs from hairpin templates to detect chloramphenicol, which is characterized in that the aptamer DNA with hairpin structure is used as template to synthesize Ag NCs, sample to be tested is mixed with Ag NCs, the presence of chloramphenicol (CAP) and the binding of aptamer DNA lead to the destruction of the hairpin structure and the partial disappearance of fluorescence, based on the change in the fluorescence of Ag NCs, it is determined that the CAP concentration to achieve CAP detection.

However, the current reports on the detection of Ag NCs are limited to the detection of substances in aqueous solutions of Ag NCs, and there are few reports on the self-assembled functional materials of Ag NCs for the detection of small molecules. To this end, the present invention is proposed.

SUMMARY

In view of the deficiencies of the prior art, the present invention relates to a Silver nanocluster ($Ag_9$-NCs) fluorescent nanotube, preparation method and its application in the detection of arginine. The $Ag_9$-NCs used in this invention is nine-core Ag NCs that does not emit light in aqueous solution when monodisperse, but due to the non-covalent interaction between $Ag_9$-NCs ligands, the charge transfer of ligands to metal, the charge transfer of ligands to metal-metal, and metal-metal interaction, $Ag_9$-NCs can have certain luminescence after being assembled. In this invention, $Ag_9$-NCs fluorescent nanotube with good photoluminescence properties at room temperature is obtained by supramolecular self-assembly of $Ag_9$-NCs under the induction of DD-5, at the same time, the $Ag_9$-NCs fluorescent nanotube has sensitivity and specificity for the detection of Arg, hence it can be used to detect Arg. The preparation method of $Ag_9$-NCs fluorescent nanotube of this invention is straightforward, meanwhile, the change of fluorescence intensity can be observed by using portable ultraviolet lamp, the operation is simple, and the realization is easy.

BRIEF DESCRIPTION

This invention presents a preparation method of $Ag_9$-NCs fluorescent nanotube and its application in the detection of Arg. The $Ag_9$-NCs fluorescent nanotubes is obtained by supramolecular self-assembly under the induction of DD-5. At the same time, prepared $Ag_9$-NCs fluorescent nanotube has specificity and sensitivity for the detection of Arg, hence that it can be used for the detection of Arg.

The technical solution of the present invention is as follows:

The $Ag_9$-NCs fluorescent nanotube is obtained through supramolecular self-assembly of $Ag_9$-NCs under the induction of DD-5.

The said DD-5 is polymerized from five aspartic acids, and the molar mass is 593.46 g·mol$^{-1}$; The $Ag_9$-NCs is nine-core Ag NCs with Ag as core and 2-mercaptobenzoic acid ($H_2$mba) as ligand. The $Ag_9$-NCs fluorescent nanotube of this present invention is obtained by non-covalent interactions such as intermolecular hydrogen-bonding, π-π stacking, and argentophilic interactions after the introduction of DD-5.

According to a preferred embodiment of the invention, the said $Ag_9$-NCs fluorescent nanotube has a diameter of 30-50 nm and a length of 5-20 μm.

According to a preferred embodiment of the invention, the fluorescence spectrum of the said $Ag_9$-NCs fluorescent nanotube shows that excitation wavelength is 400-550 nm, and emission wavelength is 550-800 nm.

According to a preferred embodiment of the invention, the fluorescence lifetime of the said $Ag_9$-NCs nanocluster nanotube is 6.10 μs, and the quantum yield is 8.11%.

According to a preferred embodiment of the invention, the preparation method of the said $Ag_9$-NCs fluorescent nanotube, which comprises steps as follows:

Disperse silver nitrate ($AgNO_3$) and $H_2$mba in water and carry out ultrasonic treatment, then add ammonium hydroxide solution ($NH_3 \cdot H_2O$) to the above mixture during ultrasonic treatment to obtain yellow and transparent $Ag_9$-NCs solution; the $Ag_9$-NCs aqueous solution was mixed with DD-5, vortexed, then allowed to stand for 8 hours in 20° C. incubator to obtain $Ag_9$-NCs fluorescent nanotube hydrogel.

According to a preferred embodiment of the invention, the concentration of aqueous solution of $AgNO_3$ dispersed in the water is 1 mmol·$L^{-1}$, the concentration of aqueous solution of $H_2$mba dispersed in the water is 1 mmol·$L^{-1}$; the molar ratio of $AgNO_3$ and $H_2$mba is 1:1. Preferably, the ultrasonic frequency of the ultrasonic treatment is 30-50 kHz, the ultrasonic power is 80 W, and the ultrasonic time is 20-30 minutes.

According to a preferred embodiment of the invention, the mass concentration of $NH_3 \cdot H_2O$ is 25%; the addition amount of $NH_3 \cdot H_2O$ is until the precipitation completely dissolved. Finally a yellow clear and transparent solution is obtained.

According to a preferred embodiment of the invention, the mixing ratio of $Ag_9$-NCs aqueous solution and DD-5 is calculated according to the molar concentration of DD-5 aqueous solution after mixing is 50-80 mmol·$L^{-1}$, and the molar concentration of $Ag_9$-NCs aqueous solution is 5 mmol·$L^{-1}$.

According to a preferred embodiment of the invention, the vortex time is 20-30 s, and the resting time is 8 hours.

According to the present invention, the DD-5 is a conventional commercial product.

According to the present invention, the application of above-mentioned $Ag_9$-NCs fluorescent nanotube is in the detection of Arg.

The principle of the invention are as follows:

The non-fluorescent $Ag_9$-NCs aqueous solution prepared by this invention at room temperature, after the introduction of DD-5, non-covalent interactions such as hydrogen-bonding, π-π stacking, and argentophilic interactions can well restrict the rotation and vibration of ligands, reducing its non-radiative relaxation, ligand-to-metal charge transfer was achieved, resulting in $Ag_9$-NCs nanotube exhibiting remarkable fluorescent properties. When a specific amino acid is added, the addition of the amino acid destroys the hydrogen-bonding between molecules, so that the non-radiative relaxation channel of the ligand is opened, and fluorescence disappears, which plays the role of detect the specific amino acid.

The beneficial effects of the invention are as follows:
1. In the present invention, $Ag_9$-NCs is noble metal cluster compound with a size of 1.35 nm, which belongs to new type of inorganic material with novel structure and unique properties; using the method of supramolecular self-assembly, DD-5 successfully induced $Ag_9$-NCs to self-assemble to construct nanotube with ordered structure, thereby realizing fluorescence emission.
2. The peptide DD-5 introduced in this present invention has better biocompatibility.
3. The microscopic morphology of fluorescence emission hydrogel prepared by this present invention can be regulated by adjusting the concentration of DD-5.
4. The fluorescent nanotube of the present invention has high selectivity and sensitivity for the detection of Arg. Detection is convenient, and the change of fluorescence intensity can be observed by using portable ultraviolet lamp, the operation is simple and easy to realize.

The material characteristics described in this invention are characterized by the following methods:
1. Transmission electron microscope (TEM). The structure of fluorescent nanotube can be observed through TEM.
2. Scanning electron microscope (SEM). The surface morphology of fluorescent nanotube can be observed by SEM.
3. Fluorescence spectroscopy. Test the fluorescence intensity of sample by fluorescence spectrofluorometer.
4. Fourier transform infrared spectra (FT-IR). The forces existing between molecules were characterized by FT-IR spectra.
5. X-ray diffraction (XRD). Characterization of possible forces by XRD.

DETAILED DESCRIPTION OF THE PREFERRED EMBODIMENTS

The invention is further described in combination with Embodiments as follows, but is not limited to that.

The raw materials used in the embodiment are conventional raw materials available on the market, including: $AgNO_3$ is purchased from Tianjin Kemeiou Chemical Reagent Co., Ltd., $H_2mba$ is purchased from Sigma-Aldrich, DD-5 is purchased from GL Biochem Ltd. (Shanghai, China), various Amino acids are purchased from Sinopharm Chemical Reagent Co., Ltd, (Shanghai, China), and are used directly without further purification before use.

Example 1

A preparation method of the $Ag_9$-NCs fluorescent nanotube, including the following steps:

(1) The Synthesis of $Ag_9$-NCs

Accurately weigh $AgNO_3$ (1 mmol, 170 mg) and $H_2mba$ (1 mmol, 155 mg) are dispersed in 6 mL of water and sonicated in KQ5200DE instrument for 20 min (80 W, 40 kHz). $NH_3 \cdot H_2O$ (25%, 0.5 mL) is added to the above mixture to obtain a yellow transparent $Ag_9$-NCs solution.

(2) Preparation of $Ag_9$-NCs Fluorescent Nanotube

Accurately weigh 20.0 mg of DD-5, dissolve it in 355 μL of tertiary water, and vortex for 30 s to fully dissolve, after complete dissolution, pipette 145 μL of $Ag_9$-NCs aqueous solution, continue to vortex for 30 s to make it evenly mixed, after mixing, the concentration of DD-5 is 70 mmol·$L^{-1}$, and then stand in 20° C. incubator for 8 hours.

Figure 1:
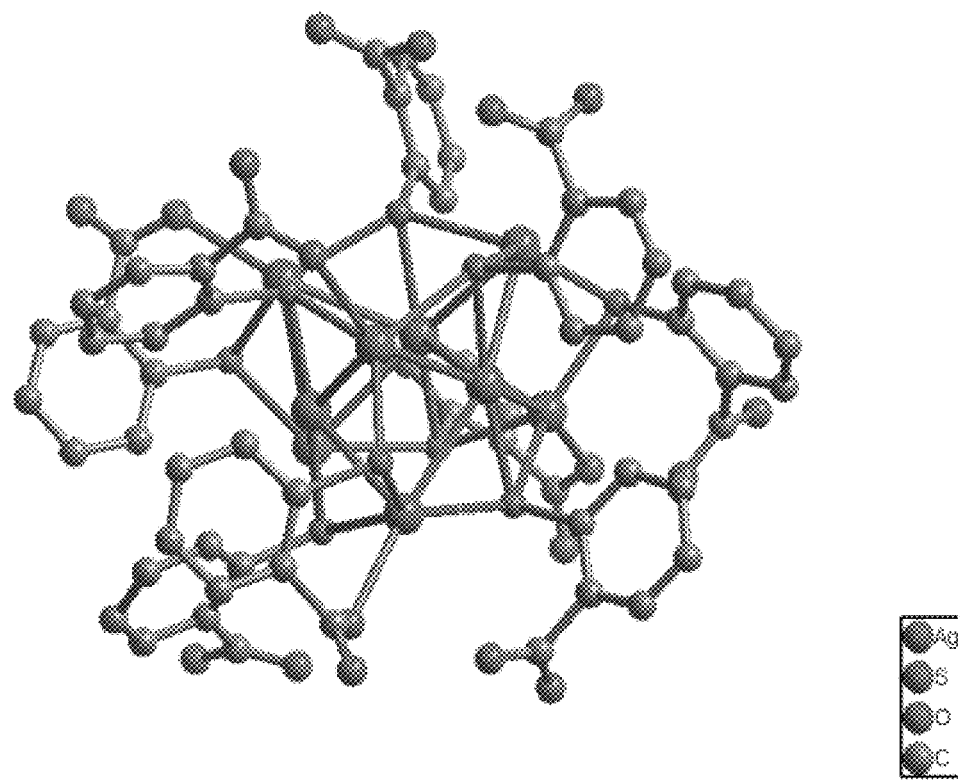
FIG. 1 is molecular structure diagram of substance $Ag_9$-NCs synthesized in Embodiment 1 of the present invention.

The molecular structure diagram of $Ag_9$-NCs obtained in this Embodiment is shown in FIG. 1. It can be seen from FIG. 1 that $Ag_9$-NCs is nine-core Ag NCs with Ag as core and $H_2mba$ as ligand.

Figure 2:
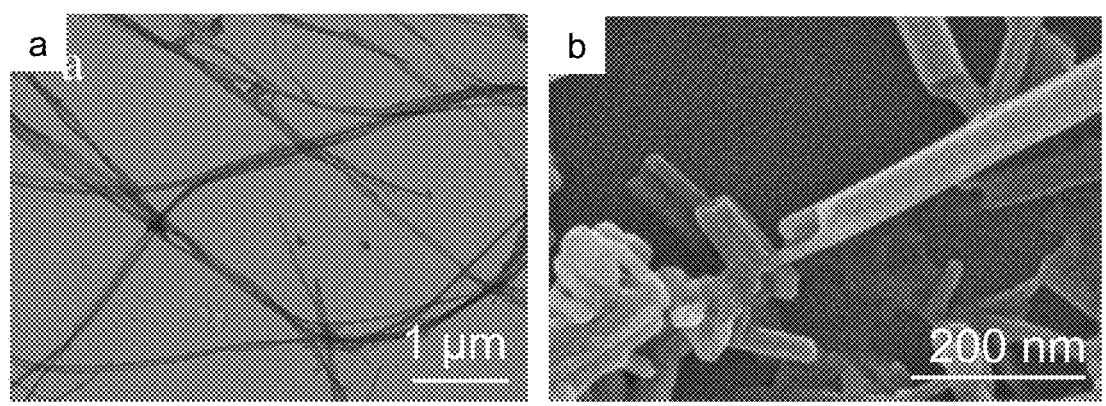
FIG. 2 are TEM and SEM images of $Ag_9$-NCs fluorescent nanotube prepared in Embodiment 1 of the present invention.

The TEM and SEM images of $Ag_9$-NCs fluorescent nanotube obtained in this Embodiment are shown in FIG. 2.

It can be seen from FIG. 2 that $Ag_9$-NCs fluorescent nanotube is in the state of nanotube, with a width of 30-50 nm and a length of 5-20 μm.

Figure 3:
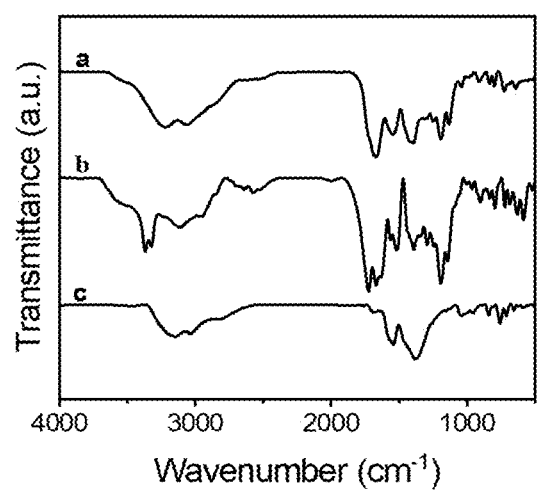
FIG. 3 is FT-IR of the fluorescent nanotube of $Ag_9$-NCs prepared in Embodiment 1 of the present invention, wherein: (a) Fluorescent nanotube, (b) DD-5, and (c) $Ag_9$-NCs.

The FT-IR of fluorescent nanotube of the $Ag_9$-NCs prepared in this Embodiment is shown in FIG. 3, and it can be seen that the formation of nanotube is mainly driven by hydrogen-bonding.

Figure 4:
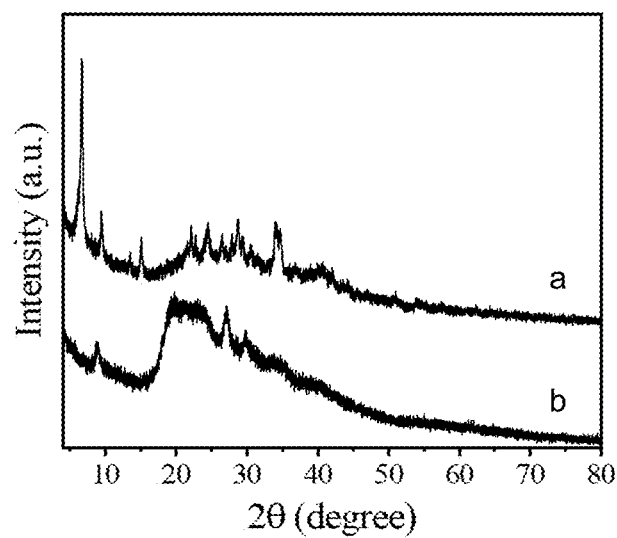
FIG. 4 is XRD pattern of the fluorescent nanotube prepared in Embodiment 1 of the present invention, wherein: (a) Fluorescent nanotube, and (b) DD-5.

The XRD pattern of $Ag_9$-NCs fluorescent nanotube prepared in this Embodiment is shown in FIG. 4, It can be seen that there is highly ordered structure in the fluorescent nanotube, and there are Ag—Ag, Ag—S and π-π interactions.

Figure 5:
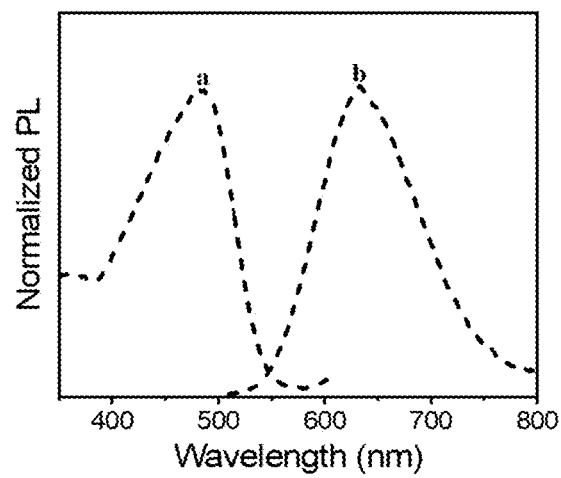
FIG. 5 is fluorescence spectrum diagram of $Ag_9$-NCs fluorescent nanotube prepared in Embodiment 1 of the present invention, wherein: (a) Excitation spectrum, (b) Emission spectrum.

The fluorescence spectrum of $Ag_9$-NCs fluorescent nanotube prepared in this Embodiment is shown in FIG. 5. It can be seen that the fluorescent nanotube has a wide excitation range with optimal excitation at 490 nm and optimal emission at 630 nm with a large Stokes shift (~140 nm).

Example 2

As described in Embodiment 1, a preparation method for $Ag_9$-NCs fluorescent nanotube includes the following steps:

Accurately weigh 14.8 mg of DD-5, dissolve it in 355 μL of tertiary water, and vortex for 30 s to fully dissolve, after complete dissolution, pipette 145 μL of $Ag_9$-NCs aqueous solution, continue to vortex for 30 s to make it evenly mixed, after mixing, the concentration of DD-5 is 50 mmol·$L^{-1}$, and then stand in 20° C. incubator for 8 hours.

The molecular structure diagram of $Ag_9$-NCs obtained in this Embodiment is shown in FIG. 1. It can be seen from FIG. 1 that $Ag_9$-NCs is nine-core Ag NCs.

Figure 6:
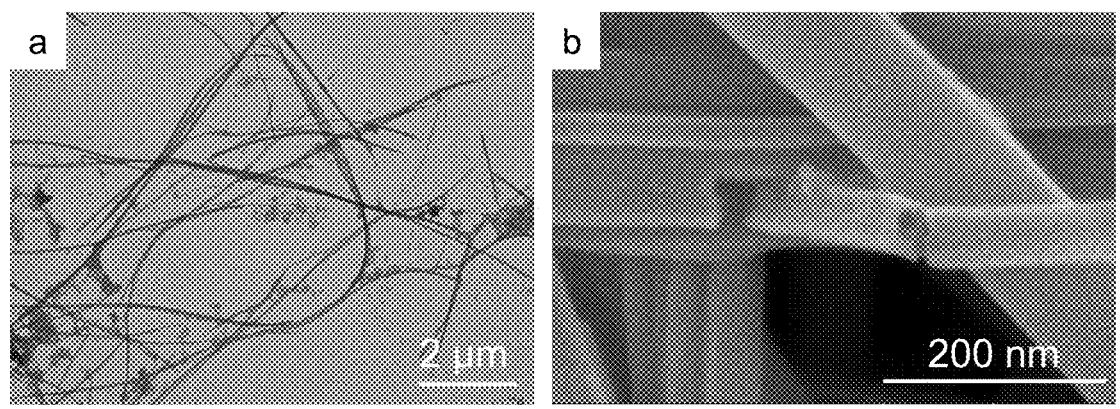
FIG. 6 are TEM and SEM images of $Ag_9$-NCs fluorescent nanotube prepared in Embodiment 2 of the present invention.

The TEM and SEM of $Ag_9$-NCs fluorescent nanotube obtained in this Embodiment are shown in FIG. 6, the $Ag_9$-NCs fluorescent nanotube is in the state of nanotube, with a width of 30-50 nm and a length of 5-20 μm.

Example 3

As described in Embodiment 1, a preparation method for $Ag_9$-NCs fluorescent nanotube includes the following steps:

Accurately weigh 17.8 mg of DD-5, dissolve it in 355 μL of tertiary water, and vortex for 30 s to fully dissolve, after complete dissolution, pipette 145 μL of $Ag_9$-NCs aqueous solution, continue to vortex for 30 s to make it evenly mixed, after mixing, the concentration of DD-5 is 60 mmol·$L^{-1}$, and then stand in 20° C. incubator for 8 hours.

The molecular structure diagram of $Ag_9$-NCs obtained in this Embodiment is shown in FIG. 1. It can be seen from FIG. 1 that $Ag_9$-NCs is nine-core Ag NCs.

Figure 7:
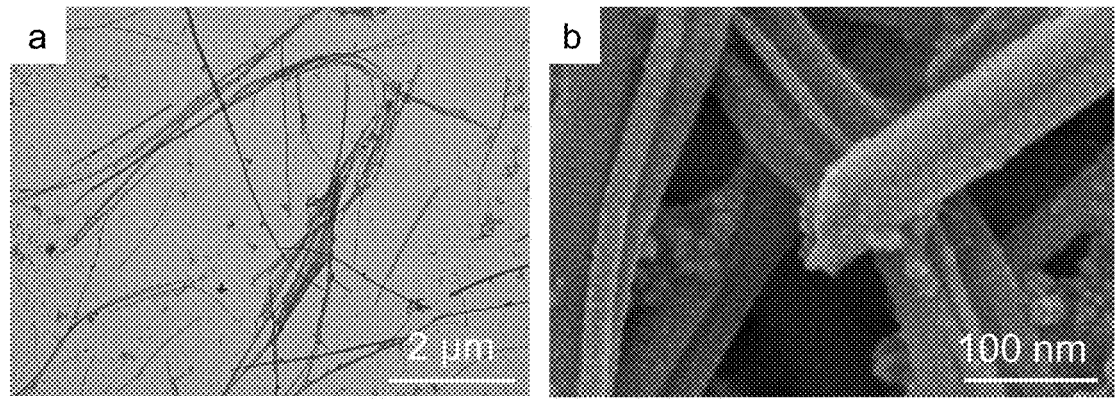
FIG. 7 are TEM and SEM images of $Ag_9$-NCs fluorescent nanotube prepared in Embodiment 3 of the present invention.

The TEM and SEM of $Ag_9$-NCs fluorescent nanotube obtained in this Embodiment are shown in FIG. 7, the $Ag_9$-NCs fluorescent nanotube is in the state of nanotube, with a width of 30-50 nm and a length of 5-20 μm.

Example 4

As described in Embodiment 1, a preparation method for $Ag_9$-NCs fluorescent nanotube includes the following steps:

Accurately weigh 23.7 mg of DD-5, dissolve it in 355 μL of tertiary water, and vortex for 30 s to fully dissolve, after complete dissolution, pipette 145 μL of $Ag_9$-NCs aqueous solution, continue to vortex for 30 s to make it evenly mixed, after mixing, the concentration of DD-5 is 80 mmol·$L^{-1}$, and then stand in 20° C. incubator for 8 hours.

The molecular structure diagram of $Ag_9$-NCs obtained in this Embodiment is shown in FIG. 1. It can be seen from FIG. 1 that $Ag_9$-NCs is nine-core Ag NCs.

Figure 8:
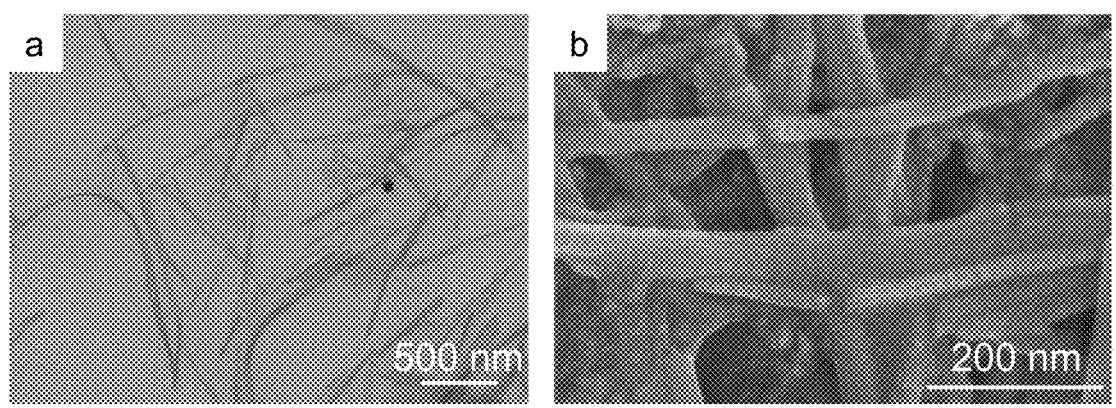
FIG. 8 are TEM and SEM images of $Ag_9$-NCs fluorescent nanotube prepared in Embodiment 4 of the present invention.

The TEM and SEM of $Ag_9$-NCs fluorescent nanotube obtained in this Embodiment are shown in FIG. 8, fluorescent nanotube is in the state of nanotube, with a width of 30-50 nm and a length of 5-20 μm.

Test Example 1

Figure 9:
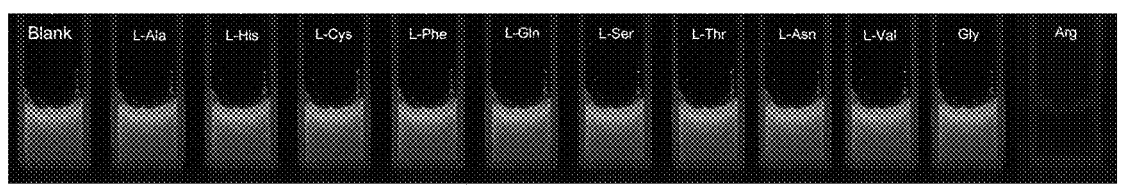
FIG. 9 are optical photographs of the sample under the irradiation of 365 nm ultraviolet lamp after adding different amino acids with the same concentration of 200 mmol·$L^{-1}$ to the fluorescent nanotube prepared in Embodiment 1 in Comparative Example 1 of the present invention.

Pipette 100 μL of amino acid (L-Arg, L-Ala, L-His, L-Cys, L-Phe, L-Gln, L-Ser, L-Thr, L-Asn, L-Val and Gly) aqueous solution with a concentration of 200 mmol·L$^{-1}$ into 100 μL of $Ag_9$-NCs fluorescent hydrogel prepared in Embodiment 1, vortex for 20 s to make it evenly mixed, and let stand for 8 hours, then observe the sample under UV lamp with a wavelength of 365 nm, as shown in FIG. 9.

Figure 10:
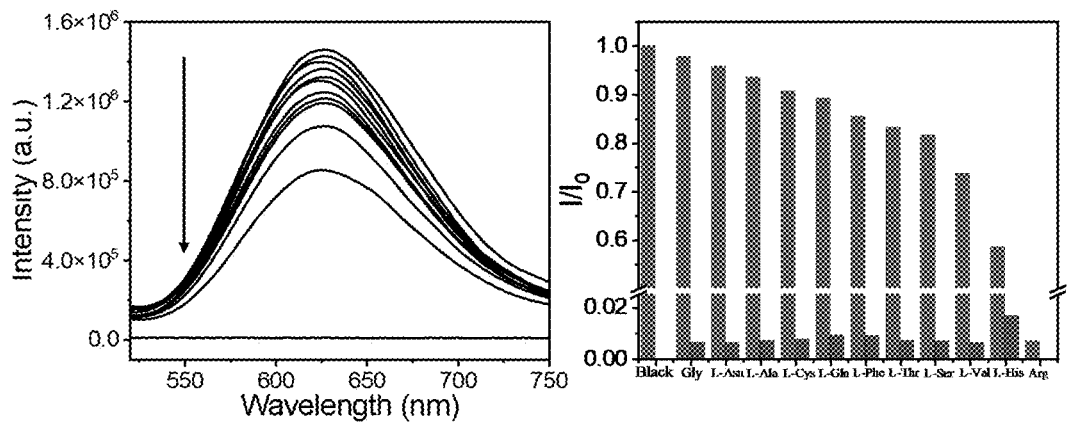
FIG. 10 are graphs showing the fluorescence properties of the fluorescent nanotube prepared in Embodiment 1 after adding different amino acids with the same concentration of 200 mmol·$L^{-1}$ in Comparative Example 1 of the present invention. Among them: the left picture is the fluorescence spectrum obtained by the sample under the excitation of 490 nm, the order from top to bottom is: Blank, Glycine (Gly), L-Asparagine (L-Asn), L-α-Alanine (L-Ala), L-Cysteine (L-Cys), L-Glutamine (L-Gln), L-phenylalanine (L-Phe), L-tyrosine (L-Thr), L-serine (L-Ser), L-valine (L-Val), L-Histidine (L-His) and L-Arginine (L-Arg); The column on the left in the right figure represents the histogram of the ratio of the fluorescence intensity at the wavelength of 630 nm after adding amino acids (I) and before adding amino acids ($I_0$) to the $Ag_9$-NCs fluorescent nanotube prepared in Embodiment 1, and the column on the right in the right figure represents the histogram of the ($I/I_0$) ratio at 630 nm after adding other amino acids to the $Ag_9$-NCs fluorescent nanotube prepared in Embodiment 1 of the present invention and continuing to add L-Arg.

The $Ag_9$-NCs fluorescent nanotube and the samples after adding different kinds of amino acids are transferred to triangular quartz cuvettes, respectively, and the emission spectra of the samples are measured using fluorescence spectrophotometer, as shown in FIG. 10 (left). The interference detection of L-Arg in $Ag_9$-NCs fluorescent nanotube is shown in FIG. 10 (right).

After the introduction of $Ag_9$-NCs in DD-5, due to intermolecular hydrogen-bonding, π-π interaction and argentophilic interactions, highly ordered aggregates are formed, which induces the AIE effect of $Ag_9$-NCs and makes it emit fluorescence. As shown in FIG. 9, 10 (left) and (right), after adding different kinds of amino acids, it can be found that L-Arg can completely quench the fluorescence, and the addition of other amino acids has little effect on the fluorescence intensity. It shows that the fluorescent nanotube prepared by the present invention has high selectivity in the detection of L-Arg. This phenomenon can be observed using both portable UV lamp and fluorescence spectrum, and the inspection results are easy to observe and measure.

Test Example 2

Figure 11:
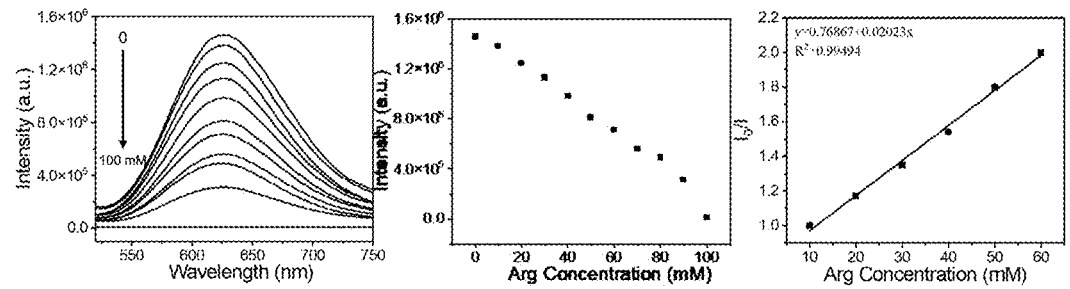
FIG. 11 is graph of the fluorescence properties after adding different concentrations of L-Arg to Embodiment 1 in Comparative Example 2 of the present invention; among them, the left picture is the obtained fluorescence spectrum, the middle picture shows the change of fluorescence intensity at 630 nm, the right figure shows the Stern-Volmer quenching curve of $Ag_9$-NCs fluorescent nanotube at 630 nm for L-Arg concentration, the fluorescence intensity at 630 nm before adding L-Arg is I, and the fluorescence intensity at 630 nm after adding L-Arg is $I_0$.

Pipette 100 μL of L-Arg aqueous solutions of different concentrations into 100 μL of the fluorescent hydrogel of $Ag_9$-NCs prepared in Embodiment 1, vortex for 20 s to make them evenly mixed, and let stand for 8 hours. The samples containing different concentrations of L-Arg are transferred into triangular quartz cuvettes, and emission spectra of the samples are measured using fluorescence spectrophotometer, and the results are shown in FIG. 11 (left). After adding different concentrations of L-Arg to $Ag_9$-NCs fluorescent nanotube, the change of fluorescence intensity at 630 nm is shown in FIG. 11 (middle). The Stern-Volmer quenching curve of $Ag_9$-NCs fluorescent nanotube at 630 nm for L-Arg concentration is shown in FIG. 11 (right).

The calculated detection limit is 330 μmol·L$^{-1}$, which indicates that $Ag_9$-NCs fluorescent nanotube prepared by the present invention has sensitivity in the detection of L-Arg.

Figure 12:
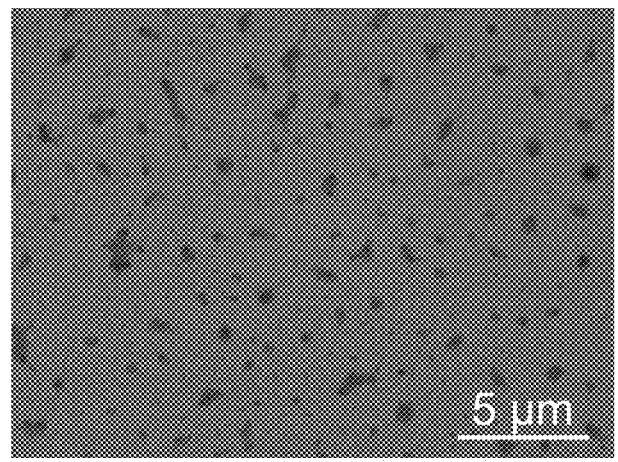
FIG. 12 is TEM image of fluorescence quenching after adding 200 mmol·$L^{-1}$ L-Arg to $Ag_9$-NCs fluorescent nanotube prepared in Embodiment 1 in Comparative Example 2 of the present invention.
Figure 13:
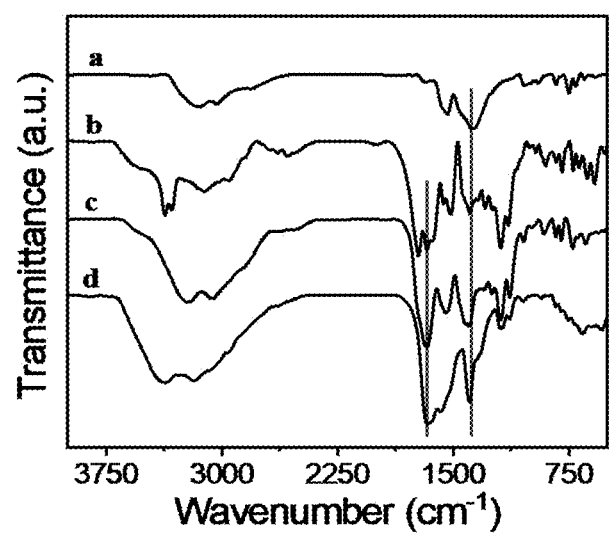
FIG. 13 is FT-IR diagram of fluorescence quenching after adding 200 mmol·$L^{-1}$ L-Arg to $Ag_9$-NCs fluorescent nanotube prepared in Embodiment 1 in Comparative Example 2 of the present invention, wherein: (a) $Ag_9$-NCs, (b) DD-5, (c) Fluorescent nanotube, (d) Fluorescent nanotube with 200 mmol·$L^{-1}$ L-Arg added.

After fluorescent nanotube prepared in Embodiment 1 are added with L-Arg and final L-Arg concentration is 100 mmol·L$^{-1}$, the obtained non-fluorescent solution is characterized by TEM, as shown in FIG. 12. Non-fluorescent solution is lyophilized into powder for FT-IR test, the results are shown in FIG. 13.

As shown in FIG. 12, after the addition of L-Arg, the highly ordered nanotube disappeared, and more particles with ultrafine nanowires appeared, indicating that the addition of L-Arg destroyed the nanotube structure. As shown in FIG. 13, after the addition of L-Arg, the stretching vibration peak belonging to the carbonyl group in $Ag_9$-NCs reappeared, and the peak of the DD-5 amide I band also reappeared, indicating that the addition of L-Arg destroyed the intermolecular hydrogen-bonding, reducing the radiative relaxation of ligand, then fluorescence disappeared.

What is claimed is:

1. A silver nanocluster ($Ag_9$-NCs) fluorescent nanotube, characterized in that, the $Ag_9$-NCs fluorescent nanotube is obtained by a supramolecular self-assembly process of $Ag_9$ under an induction of DD-5;
   wherein the DD-5 is formed by a polymerization of five aspartic acids; the $Ag_9$ is nine-nuclear Ag with Ag as core and 2-mercaptobenzoic acid ($H_2$mba) as ligand; and
   the supramolecular self-assembly process is to mix $Ag_9$ aqueous solution with DD-5, vortex, and let it stand for 8 hours in 20° C. incubator to obtain the $Ag_9$-NCs fluorescent nanotube;
   wherein the $Ag_9$ aqueous solution is produced by dispersing $AgNO_3$ and $H_2$mba in water with ultrasonic treatment, and adding $NH_3·H_2O$; and the $Ag_9$-NCs fluorescent nanotube is sensitivity to L-Arg only, which is specifically used for detecting L-Arg.

2. The silver nanocluster ($Ag_9$-NCs) fluorescent nanotube according to claim 1, characterized in that, the $Ag_9$-NCs fluorescent nanotube has a diameter of 30-50 nm and a length of 5-20 μm.

3. The silver nanocluster ($Ag_9$-NCs) fluorescent nanotube according to claim 1, characterized in that, fluorescence spectrum of the $Ag_9$-NCs fluorescent nanotube shows that excitation wavelength is 400-550 nm, and emission wavelength is 550-800 nm.

4. The silver nanocluster ($Ag_9$-NCs) fluorescent nanotube according to claim 1, characterized in that, fluorescence lifetime of the $Ag_9$-NCs fluorescent nanotube is 6.10 μs, and quantum yield is 8.11%.

5. The silver nanocluster ($Ag_9$-NCs) fluorescent nanotube according to claim 1, wherein concentration of $AgNO_3$ is 1 mmol·L$^{-1}$, and concentration of $H_2$mba is 1 mmol·L$^{-1}$; molar ratio of $AgNO_3$ and $H_2$mba is 1:1.

6. The silver nanocluster ($Ag_9$-NCs) fluorescent nanotube according to claim 1, wherein ultrasonic frequency of the ultrasonic treatment is 30-50 kHz, ultrasonic power is 80 W, and time is 20-30 minutes.

7. The silver nanocluster ($Ag_9$-NCs) fluorescent nanotube according to claim 1, wherein mass concentration of $NH_3·H_2O$ is 25%.

8. The silver nanocluster ($Ag_9$-NCs) fluorescent nanotube according to claim 1, wherein amount of $NH_3·H_2O$ added is until precipitate is completely dissolved.

9. The silver nanocluster ($Ag_9$-NCs) fluorescent nanotube according to claim 1, wherein final molar concentration of the DD-5 is 50-80 mmol·L$^{-1}$ and final molar concentration of $Ag_9$-NCs is 5 mmol·L$^{-1}$.

10. The silver nanocluster ($Ag_9$-NCs) fluorescent nanotube according to claim 1, wherein vortex time is 20-30 seconds during the supramolecular self-assembly process.

* * * * *